(12) United States Patent
List et al.

(10) Patent No.: US 8,114,029 B2
(45) Date of Patent: Feb. 14, 2012

(54) TEST SYSTEM FOR MEASURING THE CONCENTRATION OF AN ANALYTE IN A BODY FLUID

(75) Inventors: Hans List, Hesseneck-Kailbach (DE); Hans-Peter Haar, Wiesloch (DE); George Bevan Kirby Meacham, Shaker Heights, OH (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 3 days.

(21) Appl. No.: 12/619,384

(22) Filed: Nov. 16, 2009

(65) Prior Publication Data
US 2010/0094172 A1 Apr. 15, 2010

Related U.S. Application Data

(63) Continuation of application No. PCT/EP2008/056404, filed on May 26, 2008.

(60) Provisional application No. 60/940,550, filed on May 29, 2007.

(51) Int. Cl.
*A61B 5/00* (2006.01)
*A61B 17/14* (2006.01)
*A61B 17/32* (2006.01)
(52) U.S. Cl. .................. 600/583; 606/181; 606/182
(58) Field of Classification Search .............. 600/583, 600/584; 606/181, 182, 183, 184, 185, 186, 606/187, 188, 189
See application file for complete search history.

(56) References Cited

U.S. PATENT DOCUMENTS

| 4,794,926 | A  | * | 1/1989 | Munsch et al. | 606/183 |
|---|---|---|---|---|---|
| 5,286,362 | A  |   | 2/1994 | Hoenes et al. | |
| 5,871,494 | A  |   | 2/1999 | Simons et al. | |
| 6,261,245 | B1 | * | 7/2001 | Kawai et al. | 600/576 |
| 6,265,957 | B1 | * | 7/2001 | Baginski et al. | 335/266 |
| 6,646,529 | B1 | * | 11/2003 | Kahnert et al. | 335/229 |
| 7,674,232 | B2 | * | 3/2010 | Boecker et al. | 600/583 |
| 2003/0157724 | A1 |  | 8/2003 | Petrich et al. | |
| 2004/0155743 | A1 | * | 8/2004 | Sako | 335/220 |
| 2006/0047220 | A1 | * | 3/2006 | Sakata et al. | 600/583 |
| 2006/0116607 | A1 | * | 6/2006 | Nakamura et al. | 600/583 |
| 2006/0241669 | A1 | * | 10/2006 | Stout et al. | 606/182 |

(Continued)

FOREIGN PATENT DOCUMENTS

EP 1709906 A1 10/2006

(Continued)

*Primary Examiner* — Max Hindenburg
*Assistant Examiner* — Charles Becker
(74) *Attorney, Agent, or Firm* — Kristina E. Swanson

(57) ABSTRACT

An actuator for driving a test element is disclosed. The test element can comprise a lancet for perforating the skin of a living organism. The actuator can comprise an engaging part for engaging and driving the test element in a lancing motion. The actuator can further comprise a lancing actuator and a lancing spring. The lancing actuator can bias the lancing spring by executing a forward movement and thereby can exert a biasing force on the engaging part. The actuator can further comprise a latch element. The latch element can be a force-sensitive latch element for exerting a retention force to hold back the engaging part. The retention force can counteract the biasing force. The latch element can release the engaging part when the biasing force exerted by the lancing actuator exceeds the retention force exerted by the latch element, thereby allowing the test element to perform the lancing motion.

25 Claims, 11 Drawing Sheets

U.S. PATENT DOCUMENTS

| | | | |
|---|---|---|---|
| 2006/0258958 A1* | 11/2006 | Dosmann | 600/583 |
| 2007/0100255 A1* | 5/2007 | Boecker et al. | 600/583 |
| 2007/0219572 A1 | 9/2007 | Deck et al. | |
| 2008/0108910 A1 | 5/2008 | Hein et al. | |
| 2008/0188883 A1* | 8/2008 | Deck et al. | 606/182 |
| 2008/0249435 A1 | 10/2008 | Haar et al. | |
| 2010/0069943 A1* | 3/2010 | Roe | 606/181 |

FOREIGN PATENT DOCUMENTS

| | | |
|---|---|---|
| WO | 01/48461 A1 | 7/2001 |
| WO | 03/008834 A1 | 1/2003 |
| WO | 03/088834 A1 | 10/2003 |
| WO | 2005/084546 A2 | 9/2005 |
| WO | 2006/013045 A1 | 2/2006 |
| WO | 2007/006399 A1 | 1/2007 |
| WO | 2007/045412 A1 | 4/2007 |

* cited by examiner

TEST SYSTEM FOR MEASURING THE CONCENTRATION OF AN ANALYTE IN A BODY FLUID

CROSS-REFERENCE TO RELATED APPLICATIONS

This application is a continuation of PCT/EP2008/056404, filed May 26, 2008, which is based on and claims priority to U.S. Provisional Application Ser. No. 60/940,550, filed May 29, 2007, which is hereby incorporated by reference.

BACKGROUND

The present disclosure generally relates to an actuator for driving a test element and, in particular, relates to an actuator for driving a test element, wherein the test element comprises a lancet for perforating a skin portion of a living organism.

Monitoring of the concentration of certain analytes in body fluids, such as blood glucose or cholesterol, can form an essential part of the daily routine for many patients suffering from certain diseases, such as diabetes. Thus, in the latter case, the blood glucose level has to be determined several times per day in a fast and reliable way, in order to be able to take appropriate medical measures.

In order to minimize the interruptions of the daily routine of the patient, in many cases, the patient uses mobile analytic systems that are easy to transport and to handle. Thus, for example, the measurement of the blood glucose level may be performed by the patient without leaving his workplace or during his leisure activities.

Many mobile systems are known to a person skilled in the art and are commercially available. These systems may function according to several distinct principles of measurement. Therein, for example, optical and/or electrochemical measurement processes may be used, in order to determine the concentration of the constituent (i.e., the analyte) of the body fluid. Thus, for example, test elements, such as test strips, may be used, which are capable of receiving a sample (e.g., a droplet) of the body fluid to be analyzed. An example of test strips (in this case electrochemical test strips) is given in U.S. Pat. No. 5,286,362. An example of measurement systems using optical analytical methods is given in WO 01/48461. The principles of measurement disclosed in these documents, as well as the chemical substances used therein, may be applied to the present disclosure. Nevertheless, other principles and/or substances may be used.

In most cases, the test elements, which are generally designed to be disposable test elements, can form an important part of the test systems, especially for portable or mobile test systems. Typically, a diabetic uses five to seven test elements per day. In most cases, it can be important to keep the test elements clean and stored under dry conditions in order not to have the measurement affected by ingressing humidity and/or other contaminations. This holds true for test elements such as the test strips mentioned above, as well as for other disposable test elements, such as test elements comprising a lancing system for perforating a skin portion of a living organism, such as of a human patient. For example, WO 03/08834 A1 discloses a device for use with a penetrating member driver to penetrate tissue. The device includes a single disk-shaped cartridge coupled to a plurality of penetrating members and operatively couplable to a penetrating member driver. The penetrating members are movable to extend radially outward from the cartridge to penetrate tissue.

Besides test systems using separate test elements for lancing and for analysis, test systems are known with combined test elements, which are suited for the lancing or sampling action as well as for analysis of the body fluid sample generated by the lancing/sampling action. These test systems, which are commonly known as "get and measure systems" ("GAM-systems"), may be designed as described in WO 2005/084546 A2. In this reference, a body fluid sampling device is disclosed, comprising a skin-piercing element having a collection zone for receiving body fluid, wherein the device further comprises a fluid receiving means remote spaced apart from the collection zone, so that body fluid in the collection zone will not contact the fluid receiving means initially. The collection zone takes up a very small volume of body fluid of about 10 to 500 nanoliters in a very short time period. The fluid receiving means may have a test zone for performing an analytical reaction. Fluid sample from the collection zone is automatically or manually transported to the fluid receiving means to contact the fluid with the test zone.

For sampling the body fluid in GAM-systems, a controlled movement of the skin-piercing or lancing element has been shown to be of some importance. For example, EP 1 709 906 A1 describes a method and a system for sampling of body fluid, wherein a piercing element perforates the skin of a body part in forward movement and collects body fluid using a capillary structure inside the piercing element. The sampling of the body fluid may be optimized by detecting the presence of the body fluid and controlling the penetration depth.

Similarly, WO 2007/045412 A1 describes a test element for use as a disposable article for examining a body fluid comprising a piercing element for piercing a body part, a collection zone configured thereon for body fluid obtained through the puncture and at least one optical waveguide for carrying out an optical measurement in the collection zone. The collection zone is configured by a collecting aperture of the piercing element, which the aperture is elongate in the direction of piercing, and in that the optical waveguide is integrated into the piercing element so as not to be displaced and is arranged with its distal end in a proximal measuring zone of the collecting aperture.

Still, despite of the progress that has been made during the recent years with respect to GAM-systems for piercing a skin portion of a patient and for sampling a body fluid, the precise control of the penetration of the piercing or lancing system remains a major challenge. Thus, a very precise control of the lancing action is needed, such as a precise control of the penetration depth, the penetration force and the duration of the lancing movement.

Further, as indicated above, a major challenge resides in the fact that the GAM-systems as described above are rather sensitive to environmental conditions and, therefore, in many cases have to be stored in sealed compartments, such as in the system described by WO 03/088834 A1. Before initiating the lancing motion, these compartment seal barriers have to be opened by some mechanism to avoid contact between the lancing system and the compartment seal barriers. This is necessary since the lancing systems for use in GAM-systems in many cases make use of hydrophilic surfaces in order to collect body fluid. These hydrophilic surfaces, however, may deteriorate and lose part of their hydrophilic properties if they come into contact with the seal barriers. Thus, in many cases, a very complicated actuating mechanism will have to be used, which, on the one hand, allows for opening of the compartments of the test element to be used, and which, on the other hand, allows for a simple initiation of the lancing motion.

WO 2006/013045 A1 discloses a blood collection system for collecting blood for diagnostic purposes. The system comprises an electric motor, which provides energy for propelling a lancet. The blood collection system also comprises a mechanical energy accumulator, in which the electric energy that is converted by the motor is stored in the form of mechanical energy. WO 2006/013045 A1 further discloses the use of a motor for biasing a spring element. The motor current is monitored in order to monitor the compression status of the spring element, and as soon as the compression of the spring element reaches a defined state, the motor is stopped, and the spring element may be released by a separate action, in order to release the mechanical energy and in order to start the lancing motion.

WO 2007/006399 A1 discloses a lancet device by means of which a lancet can be displaced along a puncturing path in order to create a puncture wound on a skin surface, especially to obtain body fluid for diagnostic purposes. The lancet device comprises a lancet drive with a driving means generating a driving force for a puncturing movement of the lancet along the puncturing path in the direction of the skin surface. The lancet drive is provided with a magnet, with the aid of which a magnetic retaining force can be generated that acts counter to the driving force, as well as triggering means which allow the retaining force to be reduced such that the lancet is accelerated in the direction of the skin surface under the effect of the driving force generated by the driving means.

The systems disclosed by WO 2006/013045 A1 and by WO 2007/006399 A1 provide a significant improvement with regard to the control of the lancing motion. Nevertheless, both in the system disclosed by WO 2006/013045 A1 and in the system disclosed in WO 2007/006399 A1, an active triggering mechanism for triggering the lancing motion is required, which in some cases might increase the complexity of the system. Further, a precise control of the penetration depth of the lancing motion remains a challenge.

Therefore, there is a need for a simple and environmentally protected system that allows for a very precise control of the lancing motion of a lancet as well as for a precise depth control of the sampling of body fluid.

SUMMARY

According to the present disclosure, a test system comprising an actuator for driving a test element is disclosed. The test element can comprise a lancet for perforating a skin portion of a living organism. The actuator can comprise an engaging part for engaging and driving the test element to perform a lancing motion. The actuator can further comprise a lancing actuator and a lancing spring. The lancing actuator can bias the lancing spring by executing a forward movement and thereby exerting a biasing force on the engaging part. The actuator can further comprises a latch element. The latch element can be a force-sensitive latch element. The latch element can exert a retention force holding back the engaging part. The retention force can counteract the biasing force. The latch element can release the engaging part when the biasing force exerted by the lancing actuator exceeds the retention force exerted by the latch element, thereby allowing for the test element to perform the lancing motion. The actuator can allow for a very precise control of the lancing motion and for a precise control of the sampling of body fluid.

In accordance with another embodiment of the present disclosure, an opening mechanism for use in a test system for measuring the concentration of one or more constituents in a body fluid of a living organism is disclosed. The test system can comprise a test element. The test element can comprise a lancet for perforating a skin portion of the living organism. The test system can further comprise a magazine including at least one compartment. The at least one compartment can comprise at least one test element. The at least one compartment can comprise at least one barrier to preserve sterility of the test element and to exclude environmental contaminants. The opening mechanism can comprise a first opening element for opening the barrier in at least one lancing portion, allowing for the test element to perform the lancing motion without getting into contact with the barrier. The opening mechanism can comprise a second opening element for opening the barrier in at least one engagement portion The engagement portion can allow for engaging part of the test system to engage the test element. The opening mechanism can simultaneously actuate the first and second opening elements.

Accordingly, it is a feature of the embodiments of the present disclosure to provide a simple and environmentally protected system that allows for a very precise control of the lancing motion of a lancet and for a precise control of the sampling of body fluid. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
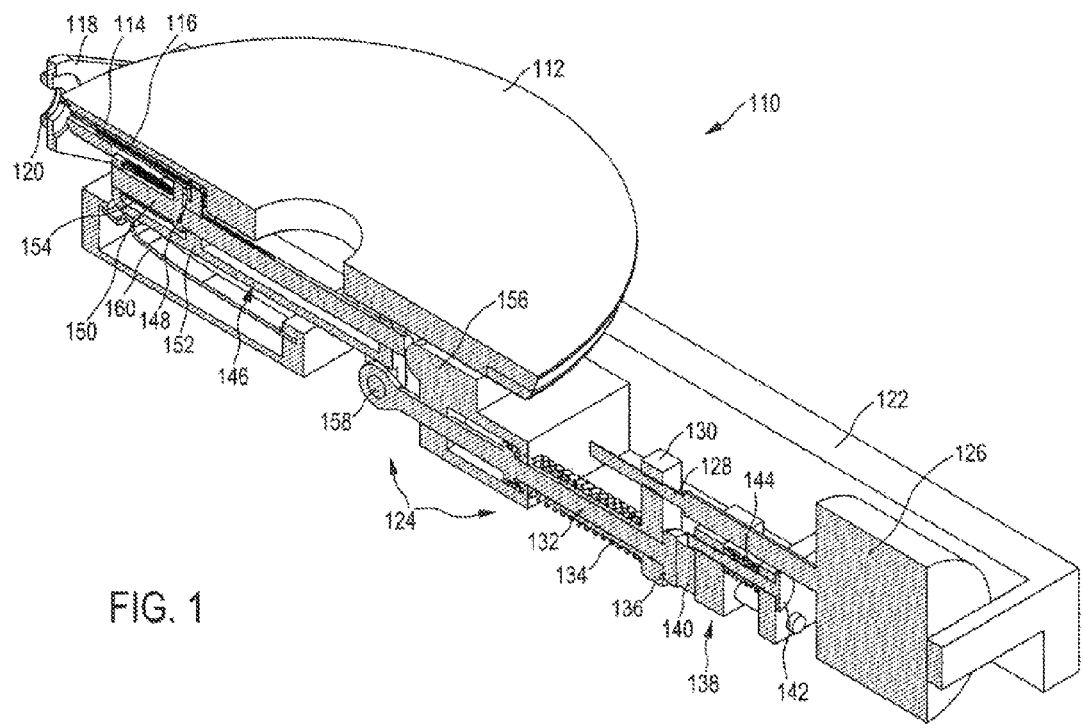
FIG. 1 illustrates a perspective view of a test system for measuring the concentration of one or more constituents in a body fluid according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An actuator for driving a test element, a test system and an opening mechanism is disclosed. The actuator is provided for driving a test element, wherein the test element comprises a lancet for perforating a skin portion of a living organism. The lancet may comprise a simple lancing needle or any other means for perforating a skin portion of a human or animal patient, such as a sharp edge etc. The actuator allows for a very precise control of the lancing motion and for a precise control of the sampling of body fluid.

The test element may comprise a simple lancet for solely perforating the skin portion, without any further sampling and/or testing means, such as a simple lancing needle without any analytical test portion. Alternatively, the test element may comprise a testing means for detecting a constituent in a fluid sample, without incorporating a lancet. Nevertheless, the test element may preferably be designed to act as a get and measure test element (such as the test elements disclosed in WO 2005/084546 A2 or WO 2007/045412 A1 which are incorporated by reference herein) and, thus, may comprise sampling and/or testing means for sampling a body fluid and for measuring the concentration of one or more constituents (also called "analytes") in the body fluid. The sampling means may comprise a capillary structure within a lancing needle. The testing means may comprise a test strip comprising one or more chemical substances for detecting the constituent. The testing means may be physically attached to the needle or may be positioned within the system, separated from the needle. An optical waveguide system may be used for optical detection of the constituent. Further, the test strip may function as sampling means, which may be connected to the needle or which may be arranged separately. Other embodiments of the test element than the embodiments described are possible, as will be obvious to the person skilled in the art.

The actuator further can comprise an engaging part for engaging and driving the test element to perform a lancing motion. A plunger may be provided, which may be capable of performing a linear motion and which may be capable of transferring momentum to the test element, in order to cause the test element to perform the lancing motion. The expression "lancing motion" may comprise a simple perforation (i.e., a unidirectional linear motion of a skin-piercing element), or may comprise further types of motion, such as a cutting motion performed by a sharp edge (e.g., a part of an edge of a knife) or a motion comprising other directional components, such as a rotational motion of a blade or a two-dimensional motion.

Instead of a plunger, many other means of engaging the test element and transferring momentum to the test element may be used. Further, the engaging part may comprise a special connection for engaging an adapted portion of the test element, in order to optimize the transfer of momentum, such as grippers, hooks, lugs, or similar means. Further, the engaging part may comprise an appropriate contact or port to the test element, in order to allow for a direct measurement of the analyte within the body fluid, as soon as a sample of the body fluid has been taken. Further examples of this engaging part will be described in more detail below.

Further, the actuator can comprise a lancing actuator and a lancing spring. The lancing actuator may be adapted for biasing the lancing spring, e.g., during a biasing phase, by executing a forward movement and thereby exerting a biasing force on the engaging part. The lancing actuator may comprise a motor, such as a servo motor and/or a stepper motor. Other types of lancing actuators may be used.

The expression "spring" as used hereinafter (such as in "lancing spring", "coupling spring", "latch bias spring" or "lift spring") may comprise any means for storing mechanical energy. Thus, the lancing spring may comprise a coil spring or any other type of spring capable of exerting a lancing force on the engaging part when compressed, such as a plate spring or a leaf spring or an elastic element, such as a rubber band or any other type of elastomeric material, or even a hydraulic or pneumatic energy storage. Any suitable combinations of various kinds of springs are possible. Similarly, the other kinds of springs mentioned hereinafter may comprise one or more of a number of various means for storing mechanical energy. The expression "linear" actuator may include other types of actuation than simple unidirectional actuations, such as, for example, two- or even three-dimensional actuations or rotational movements.

The actuator can comprise a latch element, which may be a force-sensitive latch element and which may be adapted for exerting a retention force holding back the engaging part, e.g., during the biasing phase. The holding force at least partly can counteracting the biasing force. The latch element further can be adapted for releasing the engaging part, e.g., during a lancing phase, when the biasing force exerted by the lancing actuator can exceed the retention force exerted by the latch element, thereby allowing for the test element to perform the lancing motion. In other words, the latch can be adapted for triggering the lancing motion of the test element. Thus, the linear actuator may be adapted for biasing the lancing spring during a biasing phase by executing a forward movement and thereby exerting a relatively low force on the engaging means. The force-sensitive latch element can hold back the engaging means during the relatively low force biasing phase, and then may release the engaging means when a higher force is generated, e.g., by direct contact between the linear actuator and the engaging means, such that the lancing spring may accelerate the engaging means in a forward direction during a lancing phase and thereby may allow the test element to perform the lancing motion.

The latch element may allow for an automatic or "passive" triggering of the lancing motion without any further triggering control or triggering action, such as an electronic or manual triggering. The triggering may simply occur as soon as the biasing force exceeds the retention force, which allows for a rather simple and cost-effective construction of the actuator. The biasing of the lancing spring and the triggering of the lancing motion may be part of one and the same motion of the lancing actuator, without any stopping of the lancing actuator, or without the need of switching the lancing actuator from a "biasing state" into a "triggering state". Thus, as compared to prior art, the control of the actuator may be simplified significantly, allowing for a more simple design.

The latch element may comprise a switchable magnet, such as an electromagnetic element capable of being switched on and off by appropriate electric signals (e.g., an electromagnet), or, alternatively or additionally, may comprise a permanent magnetic element, such as one or more permanent magnets. In the latter case, the holding force of the permanent magnetic element may be counteracted by a second force, and the triggering of the lancing motion may by initiated by causing the second force to exceed the magnetic holding force. Further examples of possible embodiments of the magnetic switch element will be given below. More generally, the latch element may be any of a number of mechanisms, (e.g., a mechanical decent) that can restrain the test element below a set holding force and can release the test element when this set holding force is exceeded. Additionally, the latch element may be any of a number of mechanisms, (e.g., a solenoidactuated mechanical latch) that can restrain the test element until a release signal is received from a control device.

In one embodiment, the engaging part may comprise a fast shuttle element and a slow shuttle element. The fast shuttle element may be adapted for engaging the test element. The lancing actuator may engage the slow shuttle element. The lancing spring may extend between the fast shuttle element and the slow shuttle element. The magnetic switch can be adapted for holding back the fast shuttle element. Thus, in this embodiment, the biasing force can be transferred from the lancing actuator onto the lancing spring indirectly, via the slow shuttle element. The magnetic switch element on the other hand directly can control the fast shuttle element, thereby allowing for a precise control of the triggering of the lancing motion.

In another embodiment, the magnetic switch element can comprise a magnetic element exerting an attractive magnetic force on the engaging part. The release of the engaging part can be initiated as soon as the lancing force exceeds the attractive magnetic force. In this technically simple embodiment, the magnetic switch element can be a "passive" magnetic switch element, and the triggering of the lancing motion may simply be performed by adjusting the relative position of the magnetic element and the lancing actuator.

In a further embodiment, the position of the magnetic switch element in the direction of the lancing force can be adjustable, allowing for a penetration depth of the lancing motion of the test element to be adjusted. Thus, a stroke adjustment screw may be provided, in order to allow for adjustment of the position of the magnetic switch element.

In a further embodiment, the engaging part can comprise a gripper for gripping a portion of the test element. The actuator may be adapted for at least partly transforming a linear motion of the lancing actuator into a gripping motion of the gripper. Thus, the gripper can comprise a first gripper element and a second gripper element. The first and second gripper elements can be biased by a coupling spring to exert a clamping force onto the portion of the test element. The actuator may further comprise an abutment portion. The actuator can be adapted to dislocate the first and second gripper elements by retracting the gripper and pressing one of the grippers against the abutment portion, thereby compressing the coupling spring and opening the gripper. Nevertheless, other mechanisms for opening and/or closing a gripper for engaging the portion of the test element may be provided. The actuator may be adapted to close the gripper by a forward movement of the lancing actuator.

In a further embodiment, the engaging part can comprise a pivotable portion. The pivotable portion can comprise the gripper. The actuator can be adapted to pivot the gripper into engagement with the test element by a forward movement of the lancing actuator and to pivot the gripper out of engagement with a test element by a rearward movement of the lancing actuator. The pivotable portion can be biased into engagement with the test element by a lift spring.

Generally, the actuator may be adapted for at least partly transforming a first linear motion of the lancing actuator into a second linear motion of the gripper. The second linear motion of the gripper at least can contain a directional component perpendicular to the first linear motion.

In a further embodiment, the engaging part can comprise an optical fiber connection for optically contacting the test element. Thus, the optical fiber connection can comprise an optical fiber for providing an optical excitation signal to the test element and an optical fiber for reading out an optical signal from the test element. Thus, the test element may comprise one or more substances capable of changing optical properties when in contact with a body fluid comprising the analyte. Other embodiments may be used, such as an embodiment using one or more read-out fibers but not additional excitation fibers. The expression "fiber" may comprise any element capable of guiding electromagnetic radiation, such as visible light and/or ultraviolet light and/or infrared light, from one place to another place. Thus, flexible glass fibers, flexible plastic fibers, rigid plastic or glass waveguides or any other wave guide element or combination of wave guides may be used.

Additionally or alternatively, in a further embodiment, the engaging part can comprise an electrical connection for electrically contacting the test element. These may comprise electrical elements, such as electrical ports (e.g., electrical clamps, pin-connectors, contact pads or any other contacting means) and/or electrical connectors, such as cables, wires, or other connecting means or combinations thereof may be comprised. Thus, the test element may be adapted for performing electrochemical analysis of the body fluid sample.

In a further embodiment, the actuator can be adapted to perform a retraction movement of the engaging part, thereby causing the test element to retract from a perforated skin portion. Thus, in this embodiment, the lancing motion may be supplemented and/or followed by the retraction movement. A sequence of lancing/retraction movements may be used. In one embodiment, during the retraction movement, the test element may sample body fluid from the living organism, e.g. by capillary forces. Additionally or alternatively, other types of sampling may be used, such as passive or active pump- or suction actions for sampling a body fluid, such as blood.

In a further embodiment, the actuator may be adapted for detecting if a first lancing motion resulted in a successful acquisition of a body fluid sample from the living organism. Additionally, the actuator may be adapted for re-iterating the lancing motion with an increased penetration depth if no or insufficient body fluid is acquired. This embodiment may be combined with the sampling of body fluid during the retraction movement by capillary forces.

In another embodiment, a test system for measuring the concentration of one or more constituents (analytes) in a body fluid of a living organism can be provided. The test system, which may be designed as an integrated test system for sampling and analyzing, may comprise an actuator and at least one test element. The test element can comprise a lancet for perforating a skin portion of a living organism.

In a further embodiment, the test element can further comprise a capillary transport system for acquiring a body fluid sample from the living organism. This capillary transport system may comprise one or more bores, or, alternatively or additionally, the capillary transport system may comprise one or more grooves being capable of exerting a capillary force onto the body fluid sample and thereby extracting the body fluid sample from the living organism. Alternatively or additionally, instead of using "passive" capillary forces, the capillary transport system may comprise active extraction means, such as a pump, in order to actively draw the body fluid sample from the living organism and to support the capillary forces.

In a further embodiment, the test element can further comprise a substance that changes at least one chemical or physical property as a function of a concentration of a constituent of a body fluid in contact with the substance. Thus, the substance e.g., may comprise one or more enzymes, such as gluconolactone. Examples of chemical substances which may be used with the present disclosure are described in U.S. Pat. No. 5,286,362 or in WO 01/48461. The chemical or physical property may change as a result of the simple presence of the constituent, or it may change gradually, e.g., increasingly with increasing concentration of the constituent. The chemical property, which changes with the concentration of the constituent, may comprise an electrochemical property, such as in U.S. Pat. No. 5,286,362, which may be detected electronically, or, additionally or alternatively, it may comprise an optical property, such as described in WO 01/48461, such as a color reaction, a change of reflectivity, a change in fluorescence and/or phosphorescence properties or similar optical properties.

In a further embodiment, the test system further can comprise a magazine. The magazine can comprise at least one test element. In one embodiment, the magazine can comprise at least one compartment. The at least one compartment can comprise at least one test element. The compartment may comprise at least one barrier, in order to preserve sterility of the at least one test element and to exclude environmental contaminants. The barrier may comprise a plastic foil and/or a metal foil, such as an aluminum foil, which may be used to seal the at least one compartment.

In an exemplary embodiment, the test system can further comprise an opening mechanism to open the barrier of the compartment of the test element prior to perforating the skin portion of the living organism. This opening mechanism may, for example, be designed similarly to WO 03/088834 and may prevent the test element, especially the lancet of the test element, from contacting the barrier and thereby taking risk of losing its properties, such as a potential hydrophilic property of the test element.

In one embodiment, the opening mechanism can be actuated by the lancing actuator, which allows for the opening motion and the driving of the test element to be performed by the same lancing actuator, thereby allowing for a simplification of the test system.

In another embodiment, the opening mechanism can be adapted for opening the barrier in at least one lancing portion, allowing for the test element to perform the lancing motion without contacting the barrier. Thus, the opening of the barrier in the at least one lancing portion may comprise a perforation and/or crumbling (folding) of the barrier, in order to create an opening that provides a passage for the lancet.

In a further embodiment, the opening mechanism may further be adapted for opening the barrier in at least one engagement portion. The engagement portion may allow for the engaging part of the actuator to engage the test element.

In a further embodiment, the magazine can comprise a magazine disk of substantially round shape. The disk can comprise a plurality of test elements in an essentially radial arrangement, such that the lancet of the test element can be pointing towards the outer diameter of the disk. The test system may further comprise a rotating unit for rotating the magazine disk into a sampling position with respect to a pre-selected test element. The sampling position the test system can be adapted for driving the actuator, in order to perform the lancing motion of the preselected test element. The test system may be adapted to use a new test element for each test.

In a further embodiment, an opening mechanism for use in a test system for measuring the concentration of one or more constituents in a body fluid of a living organism can be provided. The test system can comprise a test element. The test element can comprise a lancet for perforating a skin portion of the living organism. The test system can further comprise a magazine including at least one compartment. The at least one compartment can comprise at least one test element. The at least one compartment can further comprise at least one barrier to preserve sterility of the test element and to exclude environmental contaminants. The opening mechanism can comprise a first opening element for opening the barrier in at least one lancing portion, allowing for the test element to perform the lancing motion without contacting the barrier. Further, the opening mechanism can comprise a second opening element for opening the shielding in at least one engagement portion. The engagement portion can allow for engaging part of the test system to engage the test element. The opening mechanism can be adapted to simultaneously actuate the first and second opening elements.

In a further embodiment, the first and second opening elements of the opening mechanism can be one piece. Thus, the first and second opening elements may comprise a plastic or metal piece of the opening mechanism.

In a further embodiment, the first and second opening elements can be formed by edges of a pivotable opening arm. The first opening element may be arranged at a protrusion at the tip of the pivotable arm, and the second opening element may be arranged at a long side of the pivotable arm. The expression "pivotable" may comprise rotational movements and/or one- or more dimensional linear movements of the arm, and may be read as "moveable".

Turning to the figures and referring initially to FIG. 1, an exemplary embodiment of a test system for measuring the concentration of one or more constituents in a body fluid of a living organism is disclosed. In FIG. 1, a perspective sectional view of the test system 110 is illustrated. In one exemplary embodiment, the test system 110 can use a flat disk magazine 112 comprising approximately fifty test elements 114, wherein each test element can be housed in a separate compartment 116. The test elements 114 can each comprise a lancet and a measurement chemistry. The test system 110 can comprise a housing 118 including a structural base 122.

In one embodiment, the test system 110 can further comprise an actuator 124 for driving the test elements 114. In this embodiment, the actuator 124 can comprise a lancing actuator 126, which can be formed by a servo motor 126 comprising a linear drive screw 128. The linear drive screw 128 can interact with a threaded hole of a slow shuttle 130.

Further, the actuator 124 of the test system 110 can comprise a fast shuttle 132, which can be biased against the slow shuttle 130 by a lancing spring 134. A head 136 of the fast shuttle 132 can interact with a magnetic switch element 138. In one embodiment, the magnetic switch element 138 can comprise a permanent magnet 140. The position of the magnetic switch element 138 may be adjusted by a stroke adjustment screw 142, which can be biased by a latch bias spring 144.

The fast shuttle 132 can comprise an engagement member 146 for engaging the test element 114. The engaging part can comprise a gripper 148 having a first gripper element 150 and a second gripper element 152. The first and second gripper elements 150, 152 can be biased by a coupling spring 154 exerting a clamping force between the grippers 150, 152.

Further, the structural base 122 can comprise an abutment portion 156, which, by pressing against the first gripper element 150, may dislocate the first and second gripper elements 150, 152, thereby opening the gripper 158 against the clamping force of the coupling spring 154.

The engagement member 146 can be designed to be a pivotable portion, being connected to the remainder of the fast shuttle 132 by a pivot 158. Thus, the pivot 158 can allow for an up- or down-movement of the engagement member 146 comprising the gripper 158. The engagement member 146 can be biased against the disk magazine 112 by a lift spring 160.

Figure 2:
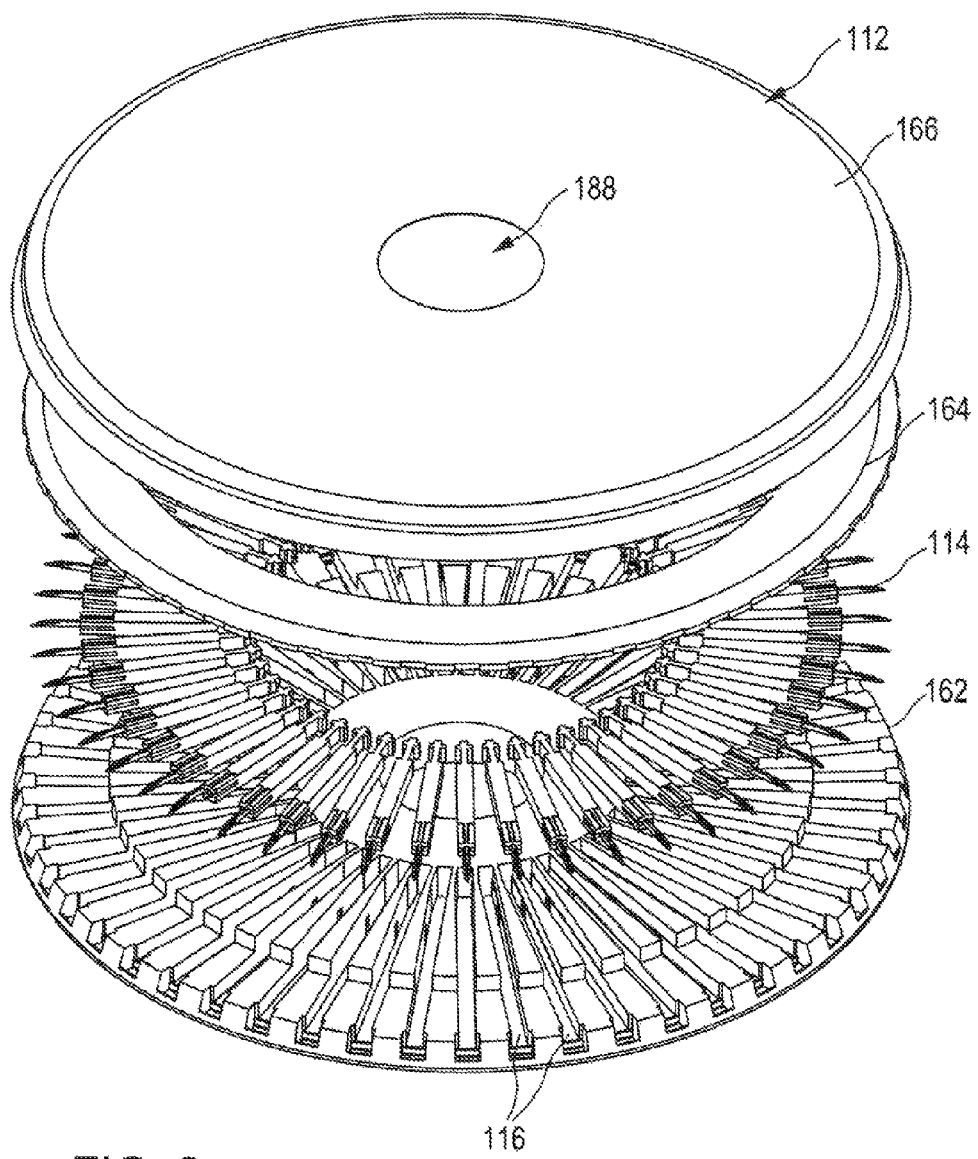
FIG. 2 illustrates an exploded view of a magazine comprising test elements according to an embodiment of the present disclosure.

In FIG. 2, an exploded view of the disk magazine 112 is shown. In this exemplary embodiment, the magazine 112 can comprise a body 162, formed by a plastic molding with radial pockets or compartments 116, comprising approximately fifty disposable test elements 114. The disk body 162 may comprise a plastic material containing a desiccant that maintains a low moisture storage environment for the measurement chemistry film of the test elements 114.

The magazine 112 can further comprise a cover ring 164, which also may be formed by a plastic molding. Further, the magazine 112 can comprise a cup-shaped foil barrier 166, which can be bonded to the bottom and the outer edge of the disk body 162 and the cover ring 164, so that each radial compartment 160 can form a separate sealed volume that can protect each disposable test element 114 from moisture and preserves its sterility. The foil may be formed by a metal, such as soft aluminum or copper, so that when it is deformed, it does not spring back. Other types of foils may be used, such as plastic foils. The disk magazine 112 and its contents may be sterilized by a penetrating process, such as an E-beam sterilization after it is sealed.

It should be noted that the exploded view of the disk magazine 112 in FIG. 2 illustrates the magazine 112 in an upside down view as compared to the disk magazine 112 shown in the test system 110 according to FIG. 1.

Figure 3:
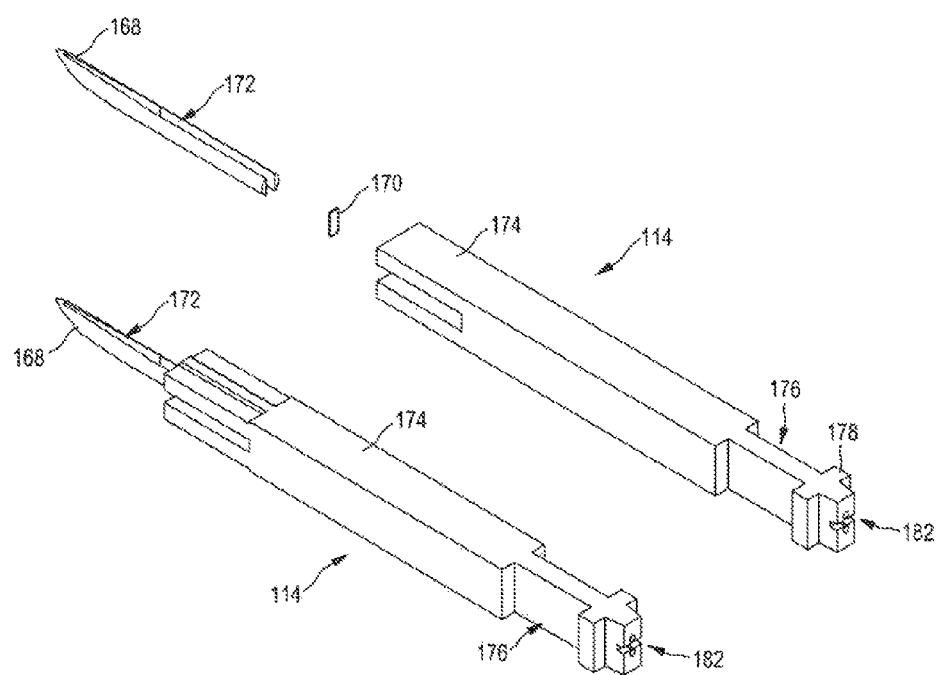
FIG. 3 illustrates a test element according to an embodiment of the present disclosure.

In FIG. 3, two test elements 114 are depicted in a perspective view. Therein, the upper test element 114 is depicted in an exploded view, in order to demonstrate the construction of the test element 114. The test elements 114 can each comprise a lancet 168, which can be formed by a slotted steel needle which may be used to penetrate the skin of a patient and to collect a small quantity of a body fluid, such as blood, in the slot, and to transport this small quantity of body fluid, driven by capillary forces, to an active surface of a glucose measurement film 170. This glucose measurement film 170 can comprise a substance, which, in this embodiment, changes its color in accordance to the concentration of the constituent of the body fluid, such as blood glucose. The slot 172 within the lancet 168 can extend to the rear end of the lancet 168, so that the lancet can comprise of two parallel slides joined at the sharp tip of the lancet 168.

The test element 114 can further comprises a test element body 174, which serves several functions and which may be formed by a plastic material. As a first function, the test element body 174 can allow for an engagement of the gripper 148 of the actuator 124, and, therefore, can comprise an engagement portion formed by gripper notches 176 near the rear end of the test element body. These gripper notches 176 can be designed to leave a rear end protrusion 178, which may be engaged by the gripper 148.

Figure 4:
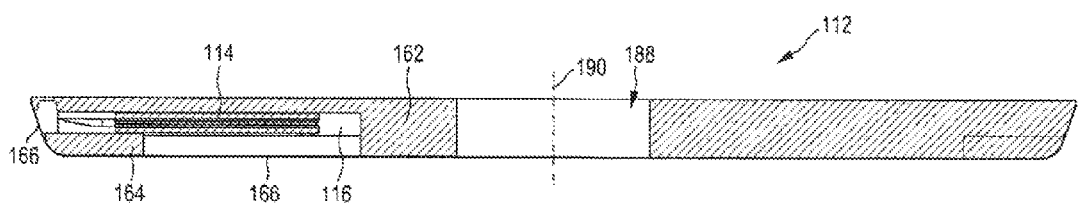
FIG. 4 illustrates a side view of the magazine shown in FIG. 2, comprising a test element according to an embodiment of the present disclosure.
Figure 5:
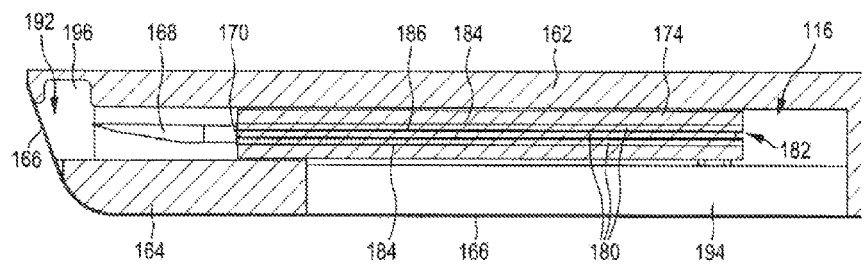
FIG. 5 illustrates an enlarged view of the test element within the magazine according to an embodiment of the present disclosure.

In FIGS. 4 and 5, an enlarged sectional side view of the magazine 112 is shown. FIG. 5 shows an enlarged view of a single compartment 116 for receiving the test elements 114. Further, as a second function, the test element body 174 can be designed to be an optical fiber slider, comprising several optical fibers. Thus, the test element body 174 can comprise three optical fibers 180, accessible by an optical port 182 at the rear end of the test element body 174. Two of the optical fibers 180 can be optical excitation fibers 184, wherein the third optical fiber can function as a readout fiber 186, which may be used to detect light emitted by the measurement film 170. In this embodiment, the engagement member 146 therefore does not only include means for mechanical engagement of the test element 114, but also optical engagement means for optically contacting the optical port 182 at the rear end of the test element 114.

As can be seen, the disk magazine 112 can comprise a central substantially circular opening 188. A rotating unit of the test system 110 (not depicted in FIG. 1) may be used in order to engage the magazine 112 by engaging the central opening 188 and thereby rotating the disk magazine 112 into a desired position, around a rotating axis 190 of the magazine 112.

The magazine compartments 116 may contain the test elements 114 each can comprise a lancing portion 192 and an engagement portion 194. The lancing and engagement portions 192, 194 both can be sealed by the foil barrier 166. The lancing portion 192 can allow for the test element 114 and the lancet 168 to leave the compartment 116, wherein the engagement portion 194 can allow for the engagement member 146 and the gripper 148 to engage the test element 114. Further, the lancing portion 192 can comprise a foil storage pocket 196 for accommodating the crumbled or folded portion of the foil barrier 166 after performing the opening process (see FIG. 8 below). The lancing portion 192 and the engagement portion 194 can be separated by the cover ring 164.

Figure 6:
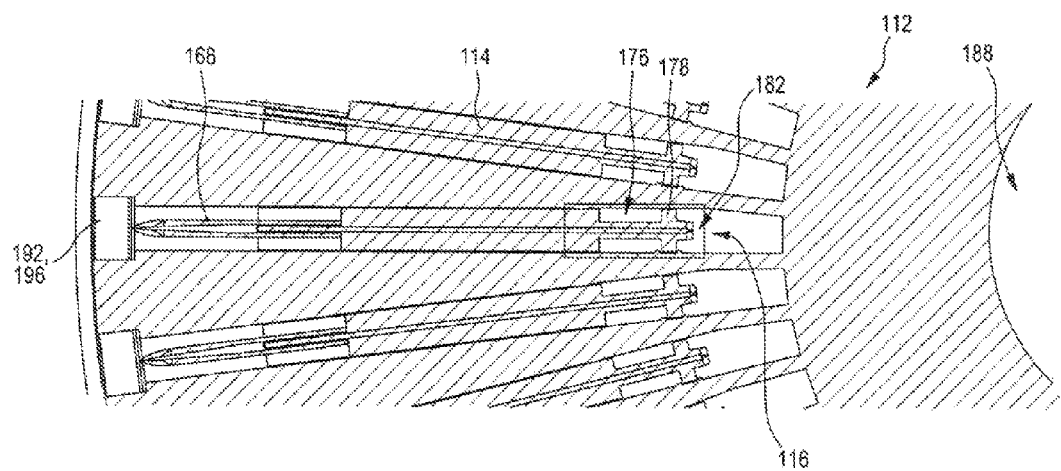
FIG. 6 illustrates a top view of the magazine shown in FIG. 2 according to an embodiment of the present disclosure.

In FIG. 6, a sectional top view of the magazine 112 is depicted. This sectional top view again shows, in addition to the perspective view in FIG. 2, the pie slice-type arrangement of the compartments 116 and the test elements 114 accommodated therein. Further, it can be seen that the lancing portion 192 of the compartments 116 can be formed to be slightly enlarged in width, as compared to the remainder of the compartments 116.

Figure 7:
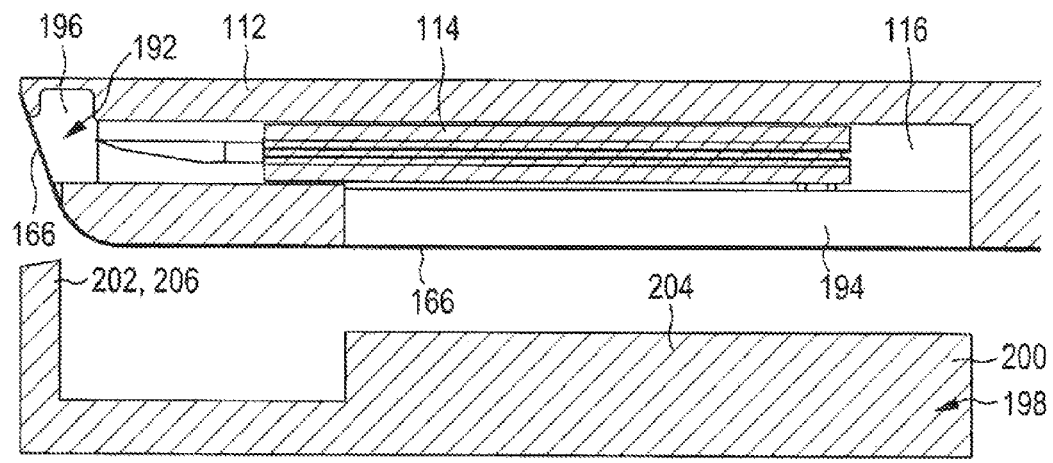
FIG. 7 illustrates a first step of interaction between an opening mechanism and the magazine shown in FIG. 2 according to an embodiment of the present disclosure.
Figure 8:
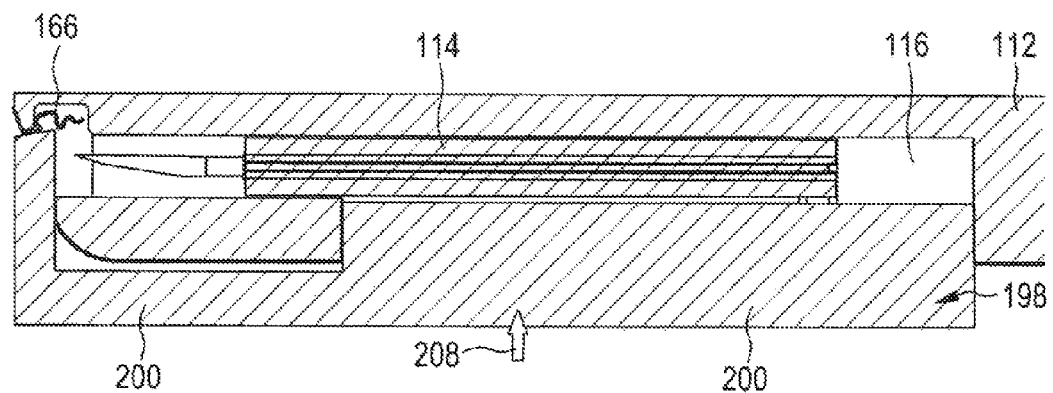
FIG. 8 illustrates a second step of interaction between the opening mechanism and the magazine according to an embodiment of the present disclosure.
Figure 9:
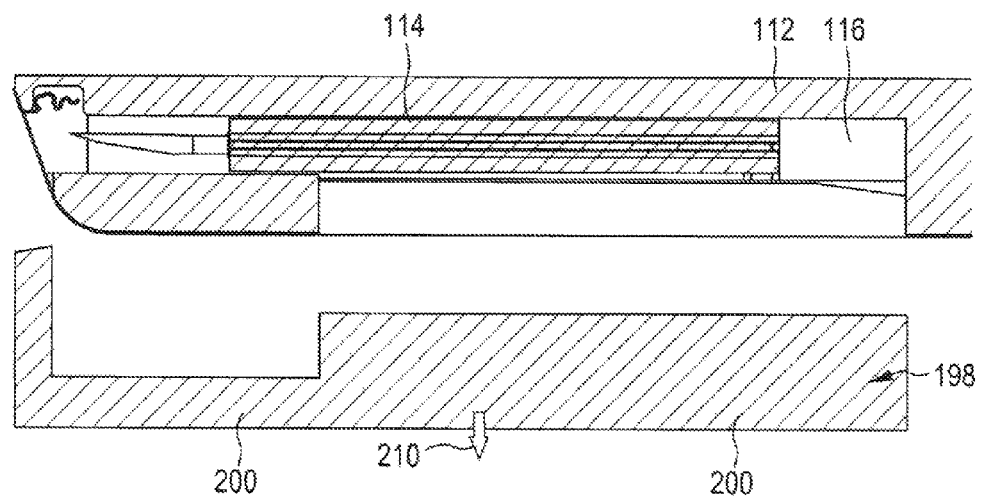
FIG. 9 illustrates a third step of interaction between the opening mechanism and the magazine according to an embodiment of the present disclosure.

In FIGS. 7 through 9, a simplified view of an opening mechanism 198 is depicted, which may be used in combination with the magazine 112 in the test system 110 according to FIG. 1. Thus, the opening mechanism 198 may be used in combination with the actuator 124, depicted in FIG. 1, and may even be driven by the actuator 124 itself. The opening mechanism 198 can be used for opening one specific compartment 116 of the disk magazine 112, in order to allow for a lancing movement of the test element 114 by moving the test element 114 linearly through the lancing portion 192 of the compartment 116 and through the opening 120 within the housing 118 by avoiding the tip of the lancet 168 touching the foil barrier 166. For this purpose, besides the sampling position of the test element 114 to be used, as depicted in FIG. 1, a separate opening position may be provided, in which the opening mechanism 198 can open the foil barrier 166 of the compartment 116 containing the test element 114 to be used in an upcoming sampling step.

The opening mechanism 198 can comprise a pivotable opening arm 200, which, in this embodiment, can be formed as single piece, but which may also be formed by two separate pieces. The opening arm 200 can comprise a first opening element 202 for opening the foil barrier 166 in the region of the lancing portion 192 and a second opening element 204 for substantially simultaneously opening the foil barrier 166 in the range of the engagement portion 194. The first opening element 202 can be formed by a sharp edge of a protrusion 206 at the front end of the opening arm 200. The second opening element 204 can be formed by edges in a linear portion of the pivotable opening arm 200.

In FIG. 8, the opening action exerted by the opening mechanism 198 is shown. For this purpose, the pivotable opening arm 200 can perform a substantially upward movement, towards the interior of the compartment 116. Thus, from FIG. 8, it can be clear that the expression "pivotable" is not limited to pure pivoting movements, but may also comprise other movements, such as the linear movement shown in FIG. 8.

During the upward movement, which, in FIG. 8, is referred to by referential 208, in one single movement, the foil barrier 166 can be opened more or less simultaneously in the lancing portion 192 and in the engagement portion 194. In the lancing portion 192, the foil barrier 166 can be cut and crumpled in the foil storage pocket 196, leaving a more or less rectangular opening in the foil barrier 166 at the front end of the test element 114, allowing for the lancet 168 to leave the compartment 116 without touching the foil barrier 166. Since no contact between the lancet 168 and the foil barrier 166 occurred during a lancing motion of the test element 114, no detrimental effects such as a deterioration of the hydrophilic properties of the lancet 168 may occur.

The opening of the foil barrier 166 in the range of the engagement portion 194, forming a long substantially rectangular or slit-like opening, can allow for the engagement member 146 to engage the test element 114. The rectangular area foil barrier can be cut on the two short sides and one long side so that an attached flap can be formed. The flap can then be folded to one side to provide free access to the engagement portion 194 of the test element 114.

After performing the opening procedure, the opening arm 200 can perform, as can be seen in FIG. 9, a substantially downward movement 210, allowing for the rotating mechanism to rotate the freshly opened compartment 116 into a sampling position, as depicted in FIG. 1.

In FIGS. 10 through 17, a number of sectional side views of the test system 110 are shown in different steps of operation, which can be used in order to explain the functioning of the test system 110 and the actuator 124.

Figure 10:
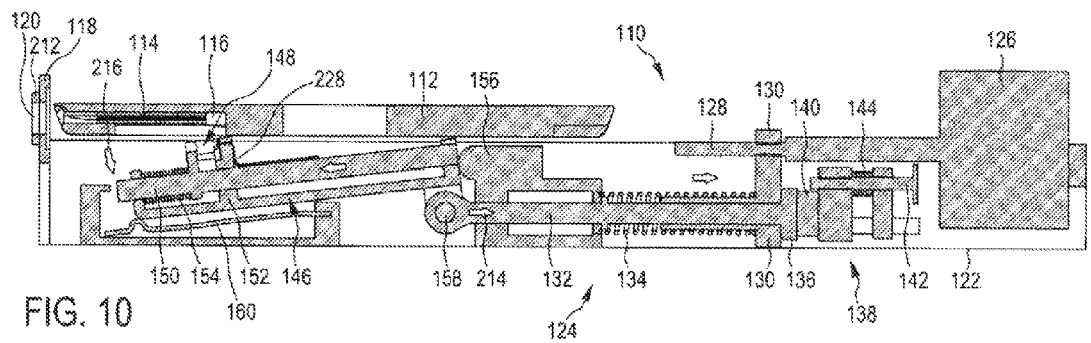
FIGS. 10-17 illustrate several steps of an operating cycle of the test system shown in FIG. 1 in a sectional view according to an embodiment of the present disclosure.

In FIG. 10, the test system 110 is depicted with the compartment 116 of the test element 114 to be used in the sampling position, with the lancet 168 pointing towards the opening 120 in the housing 118. The opening 120 can be surrounded by a rubber ring 212. The test element 114 to be used in the upcoming process may be moved by a rotating unit (not depicted) into the position depicted in FIG. 10 after performing the opening process depicted in FIGS. 7-9.

In the reset position, depicted in FIG. 10, the lancing actuator 126 can pull back the slow shuttle 130 and, by force of the lancing spring 134, the fast shuttle 132. The direction of this rearward movement is referred to by referential 214 in FIG. 10.

By this rearward movement, the rear end of the first gripper element 150 of the pivotable engagement member 146 can be pressed against the abutment portion 156. Thereby, a torque can be exerted on the pivotable engagement member 146, and a downward movement 216 of the front end of the engagement member 146 can occur by pivoting around the pivot 158, against the spring force of the lift spring 160. Simultaneously, the relative position of the first and second gripper elements 150, 152 can be changed by pressing the first gripper element 150 against the abutment portion 156, thereby opening the gripper 148. In this reset position depicted in FIG. 10, the disk magazine 112 may be rotated, in order to transport the test element 114 to be used into the sampling position.

Figure 11:
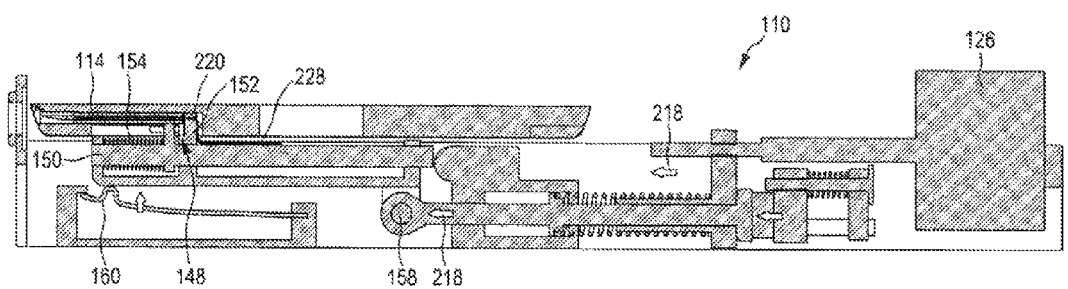

In a second process step, as depicted in FIG. 11, the test system 110 is in an engaged position. For this purpose, the lancing actuator 126 can perform a forward movement 218, thereby pivoting the gripper 148 into the compartment 116 of the test element 114. The upward movement of the gripper 148 can be supported by the lift spring 160. Further, by relaxation of the coupling spring 154, the gripper 148 can be closed, whereby a mechanical engagement between the rear end protrusion 178 of the test element 114 (see FIG. 3) and the gripper 148 can be provided. Further, the second gripper element 152 can comprise a fiber port 220, which, in the engaged position depicted in FIG. 11, can provide an optical contact to the optical port 182 at the rear end of the test element 114 (see FIG. 3), allowing for an optical readout of the measurement film 170 within the test element 114.

Figure 12:
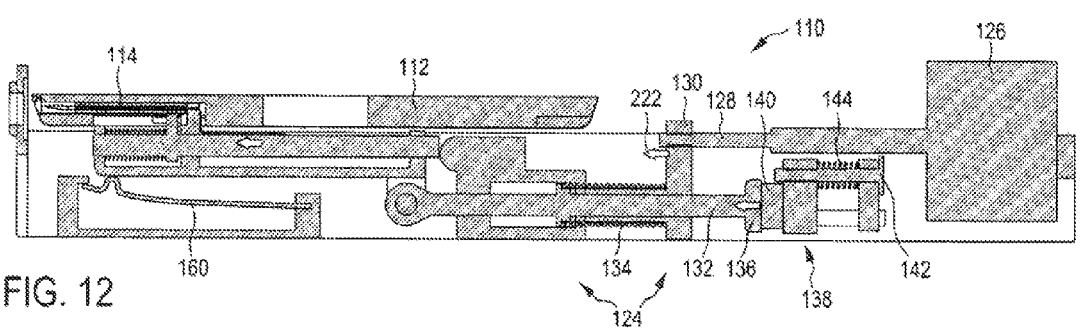

In FIG. 12, a cocked position of the test system 110 and the actuator 124 is depicted. In order to reach this cocked position, the lancing actuator 126 can push, by force of the linear drive screw 128, the slow shuttle 130 into a forward direction (in FIG. 12 referred to by referential 222). The fast shuttle 138, on the other hand, can be held back by the magnet 140, exerting a magnetic force onto the head 136 of the fast shuttle 132. Thus, by the relative movement of the slow shuttle 130 and the fast shuttle 132, the lancing spring 134 can be compressed.

When the lancing spring 134 is fully compressed, the slow shuttle 130 can contact the fast shuttle 132 and can push it out of engagement with the magnet 140. This can release the fast shuttle 132 and can start the lancing action.

Thus, by the position of the magnetic switch element 138 and the magnet 140, the triggering point of the lancing action of the test system 110 and, thus, the penetration depth of the lancet 168 of the test element 114 may be controlled. This position may be adjusted by the stroke adjustment screw 142.

Figure 13:
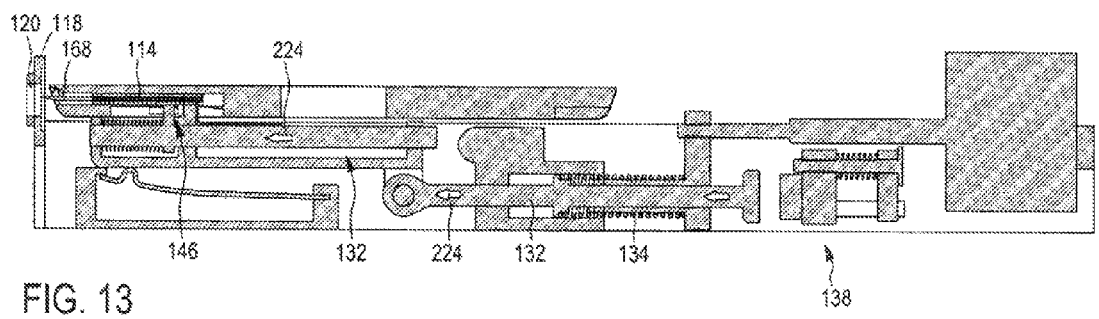

In FIG. 13, the lancing action is shown in progress. The lancing spring 134 can expand and accelerates the fast shuttle 132. Thus, the fast shuttle 132 can perform a fast forward movement, which is referred to in FIG. 13 by referential 224. Since the test element 114 can be engaged by the engagement member 146, the fast forward movement 224 of the fast shuttle 132 can be transferred to the test element 114, which therefore can perform the lancing movement, allowing for the lancet 168 to leave the housing 118 through the opening 120, in order to penetrate a skin portion of the patient.

Figure 14:
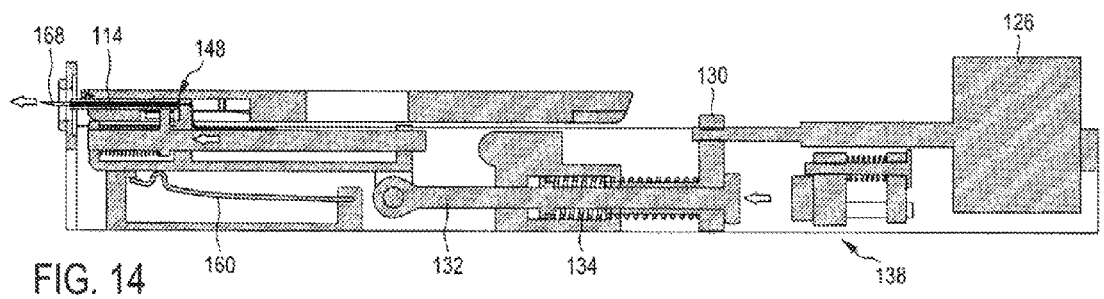

In FIG. 14, the test system 110 is shown with the test element 114 and the lancet 168 in fully extended position. The lancet 168 can extend to the desired penetration depth set by the stroke adjustment screw 142. By moving the magnetic switch element 138 rearward (towards the lancing actuator 126), the penetration depth can be lowered, whereas by moving the magnetic switch element 138 forward, i.e., away from the lancing actuator 126, the penetration depth of the lancet 168 can be increased. The movement of the fast shuttle 134 may be stopped by contact with the slow shuttle 130. An optical sensor, a motor current sensor or other means may be used to detect the lancet release and stop the advancement of the lancing actuator 126 during or shortly after the fast shuttle 134 hits the slow shuttle 130. Thus, in the position depicted in FIG. 14, a first penetration of the skin can be achieved.

Figure 15:
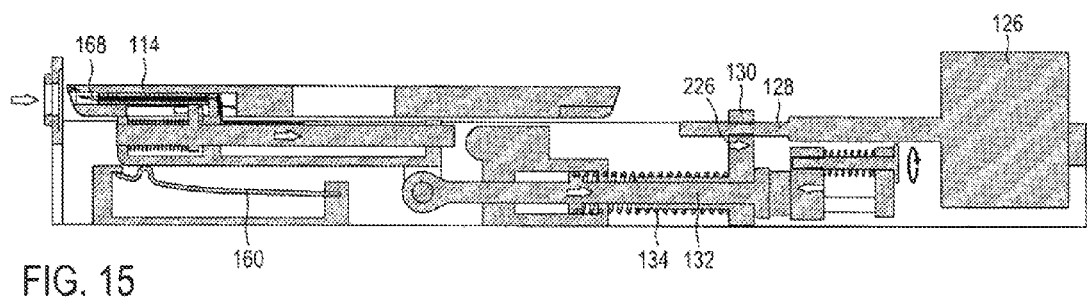

In FIG. 15, a withdrawal of the lancet 168 from the perforated skin portion is depicted. The lancing actuator 126 can perform a rearward movement 226 of the linear drive screw 128, thereby causing the slow shuttle 130 to perform a rearward movement as well. The lancing actuator 126 can control the position of the lancet 168 after maximum penetration and can enable a variety of retraction programs. A slow retraction and a detection light pulse at a sample collection position with the lancet 168 still partially in the skin can be only one possibility.

During this retraction movement of the lancet 168, blood or a similar body fluid can be collected through the slot 172 in the lancet 168. If no blood is detected by an optical detector in contact with the fiber port 220, the lancing actuator 126 may advance the slow shuttle 130 again, in order to re-cock the lancing spring 134.

Figure 16:
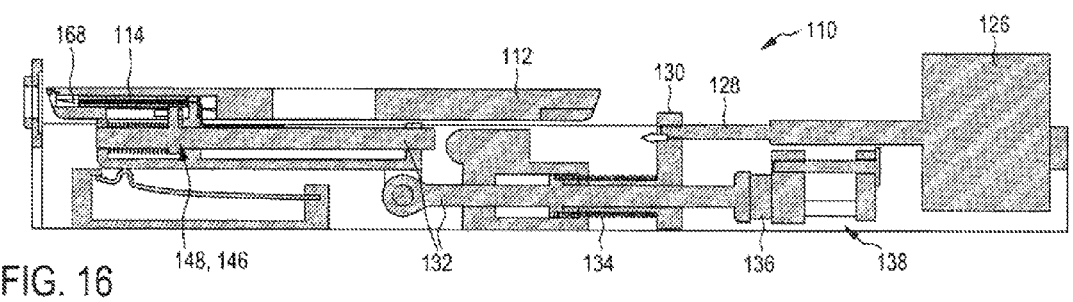

A mechanism may be used to change the penetration adjustment screw 142, in order to increase the lancet penetration depth on a following, second lancing action. As before, the fast shuttle 132 can be held back by the magnet 136 of the magnetic switch element 138. When the lancing spring 134 is fully compressed, the slow shuttle 130 can again contact the fast shuttle 132 and can push it out of engagement with the magnet 136. This can release the fast shuttle 132 and can start a second, deeper lancing action. This second cocked position is depicted in FIG. 16, which more or less corresponds to FIG. 12, but with the magnet 136 and the magnetic switch element 138 moved further to the left (compare FIGS. 12 and 16).

Figure 17:
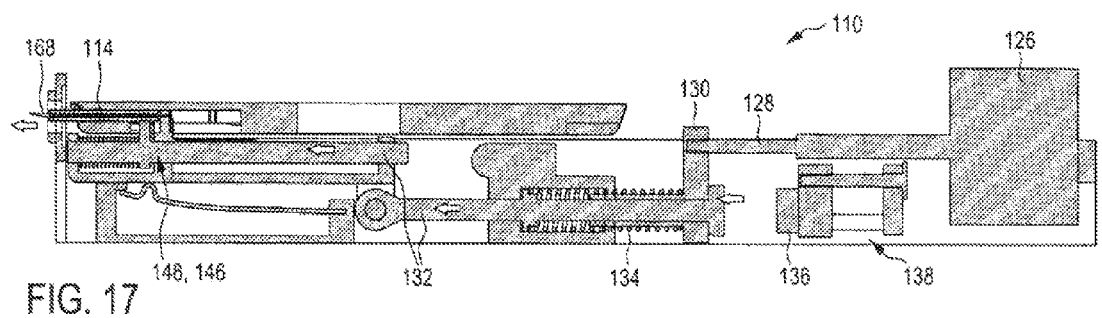

In FIG. 17, the second, optional penetration, which may be performed if no blood is detected by the test system 110, is depicted. This view more or less corresponds to the situation depicted in FIG. 14, except for the position of the magnetic switch element 138, which, according to the increased penetration depth, can be moved forward, i.e. to the left in FIG. 17, in order to increase the penetration depth. After penetration, the lancet 168 can then be retracted by the lancing actuator 126, and the mechanism can be returned to the engaged position shown in FIG. 11. If no blood is detected, then the lancet 168 may be extended slowly for manual sample collection. After the measurement is complete, the lancing actuator 126 may return the mechanism to the reset position shown in FIG. 10.

The test system 110 depicted in FIG. 1 may further comprise one or more evaluation elements for evaluating the measurement and/or for controlling the operation of the overall test system 110. Thus, the test system 110 may comprise one or more electronic components as well as one or more computer systems, for providing excitation signals to the optical port 182, as well as reading out detection signals from the optical fibers 180. Further functions may be performed by this system. Further, the movement of the overall actuator 124, specifically of the lancing actuator 126, may be controlled. Thus, the lancing actuator 126 may be driven to move the slow shuttle 130 at speeds up to about 0.1 m/s. For the lancing movement of the lancet 168, driven by the lancing spring 134, velocities of approximately 1.0 m/s may be achieved.

The test system 110 may further comprise one or more energy storage devices, such as batteries, accumulators or similar devices. Thus, e.g., a lithium primary battery may be used, such as a battery used in digital cameras. Other solutions for providing the energy required for operating the actuator 124 and/or the measurements may be used.

Further, instead of the servo motor, other types of lancing actuators 126 may be used, which may provide for a controlled forward and/or backward movement of the slow shuttle 130. The combination of the energy storage by the lancing spring 134 with the slow movement of the lancing actuator 126 can provide a fast penetration motion, despite of the potential use of a slower motor that can cock the energy storage spring 134 prior to the fast penetration motion, wherein the lancing actuator can control the test element position during subsequent sample collection and measurement steps.

The test system 110 may further comprise one or more light sources, such as light emitting diodes (LEDs) or laser diodes. These light sources may be located on a stationary structure, such as a printed circuit board, e.g., in contact with or affixed to the structural base 122. Further, one or more light detectors may be used, which may also be located inside the test system 110, e.g., on the same printed circuit board, in order to provide for the required signals for the determination of the concentration of the analyte. Light signals may be provided to the fiber port 220 and the optical port 182 via flexible optical fibers, which are denoted by referential 228 in FIGS. 10 and 11, and which are only schematically depicted. Other types of flexible light guides may be used instead of optical fibers. The optical light sources may be located on the moving optical coupling in the measuring instrument, and electrical power may be supplied from the stationary portion of the test system 110 through flexible electrical conductors. Similarly, the optical light detectors may be located on the moving optical coupling, whereas the electrical power and signal connections can be made to the stationary portion of the test system 110 through flexible electrical conductors. In a further embodiment, the optical light sources may be located on a stationary structure in the test system 110, and the light may be conveyed from the moving test element through flexible light guides.

In summary, the actuator, the test system and the opening mechanism according to one or more of the embodiments disclosed above can provide a large number of advantages over actuators, test systems and opening mechanisms as known from prior art. Thus, for lancing, sampling and preparation of measurements in get and measure systems, one simple common operation may be provided and may be sufficient for obtaining a measurement result. This operation may be realized by actuators and combined motions, wherein the switching between different motions may be provided by a latch element, in particular the magnetic switch element (magnetic latch). Further, the test system and the actuator according to one or more of the embodiments outlined above, may allow for a precise control of the lancing and/or perforation depth. The present disclosure further may allow for repetition of the lancing and/or measurement. Further, the test system and/or the actuator may allow for a "conventional" application of the body fluid sample (e.g. a blood droplet) onto the test element.

The test system may be designed as a compact, self-contained hand-held device. The test system may comprise a housing accommodating the system components. The test system may further comprise means for measurement, such as electronics and/or computer components, in order to perform a measurement of the concentration of the constituent or analyte within the body fluid. Further, input and/or output means may be provided, such as a display, keys for operating the test system, an interface for interfacing the test system with one or more computers for the purpose of control of the measurement and/or a data exchange, as well as other appropriate controls of test systems, as known from prior art systems. Further, the test system may comprise one or more energy storage elements, such as batteries, accumulators, supercapacitors and/or similar elements. Additionally or alternatively, the test system may comprise an external power supply.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An actuator for driving a test element, the test element comprises a lancet for perforating a skin portion of a living organism and the actuator comprising:
   an engaging part for engaging and driving the test element to perform a lancing motion;
   a lancing spring;
   a lancing actuator, wherein the lancing actuator biases the lancing spring by executing a forward movement and thereby exerting a spring biasing force on the engaging part; and
   a latch element, wherein the latch element is force-sensitive and exerts a magnetic retention force to hold back the engaging part that is parallel to the spring biasing force, wherein the magnetic retention force counteracts the spring biasing force, and wherein the latch element releases the engaging part when the spring biasing force exerted by the lancing actuator exceeds the magnetic retention force exerted by the latch element, thereby allowing the test element to perform the lancing motion.

2. The actuator according to claim 1, wherein the engaging part comprises,
   a fast shuttle element, wherein the fast shuttle element engages the test element and is held back by the latch element; and
   a slow shuttle element, wherein the slow shuttle element is engaged by the lancing actuator, and wherein the lancing spring extends between the fast shuttle element and the slow shuttle element.

3. The actuator according to claim 1, wherein the latch element comprises a mechanical detent.

4. The actuator according to claim 1, wherein the latch element comprises a magnetic switch element.

5. The actuator according to claim 4, wherein the magnetic switch element comprises,
   a magnetic element exerting an attractive magnetic force on the engaging part, wherein the release of the engaging part is initiated as soon as the lancing force exceeds the attractive magnetic force.

6. The actuator according to claim 1, wherein the position of the latch element in the direction of the lancing force is adjustable allowing for a penetration depth of the lancing motion of the test element to be adjusted.

7. The actuator according to claim 6, further comprising a stroke adjustment screw allowing for adjustment of the position of the latch element.

8. The actuator according to claim 1, wherein the engaging part comprises a gripper for gripping a portion of the test element.

9. The actuator according to claim 8, wherein the gripper comprises
   a first gripper element; and
   a second gripper element, wherein the first and second gripper elements are biased by a coupling spring to exert a clamping force, wherein the actuator further comprises an abutment portion, wherein the actuator dislocates the first and second gripper elements by retracting the gripper and pressing one of the grippers against the abutment portion, thereby compressing the coupling spring and opening the gripper.

10. The actuator according to claim 9, wherein the actuator closes the gripper by a forward movement of the lancing actuator.

11. The actuator according to claim 8, wherein the actuator at least partly transforms a linear motion of the lancing actuator into a gripping motion of the gripper.

12. The actuator according to claim 8, wherein the engaging part comprises
   a pivotable portion comprising the gripper, and wherein the actuator pivots the gripper into engagement with the test element by a forward movement of the lancing actuator and pivots the gripper out of engagement with the test element by a rearward movement of the lancing actuator.

13. The actuator according to claim 12, wherein the pivotable portion is biased into engagement with the test element by a lift spring.

14. The actuator according to claim 8, wherein the actuator at least partly transforms a first linear motion of the lancing actuator into a second linear motion of the gripper, wherein the second linear motion of the gripper at least contains a directional component perpendicular to the first linear motion.

15. The actuator according to claim 1, wherein the engaging part comprises an electrical connection for electrically contacting the test element.

16. The actuator according to claim 1, wherein the actuator detects if a first lancing motion resulted in acquiring of a body fluid sample from the living organism, wherein the actuator re-iterates the lancing motion with an increased penetration depth if no or insufficient body fluid is acquired.

17. A test system for measuring the concentration of one or more constituents in a body fluid of a living organism, wherein the test system comprises an actuator according to claim 1 and at least one test element, wherein the test element comprises a lancet for perforating a skin portion of a living organism.

18. The test system according to claim 17, wherein the test element further comprises a capillary transport system for acquiring a body fluid sample from the living organism.

19. The test system according to claim 17, wherein the test system further comprises
   a magazine comprising at least one test element, at least one compartment comprising a test element and at least one barrier to preserve sterility of the test element and to exclude environmental contaminants; and
   an opening mechanism to open the barrier of the compartment of the test element prior to perforating the skin portion of the living organism.

20. The test system according to claim 19, wherein the opening mechanism is actuated by the lancing actuator.

21. The test system according to claim 19, wherein the opening mechanism opens the barrier in at least one lancing portion allowing for the test element to perform the lancing motion without getting into contact with the shielding.

22. The test system according to claim 21, wherein the opening mechanism further opens the barrier in at least one engagement portion, wherein the engagement portion allows for the engaging part to engage the test element.

23. The test system according to claim 19, wherein the magazine comprises a magazine disk of an substantially round shape, wherein the disk comprises a plurality of test elements in an essentially radial arrangement, such that the lancet of the test elements are pointing towards the outer diameter of the disk.

24. The test system according to claim 23, wherein the test system further comprises a rotating unit for rotating the magazine disk into a sampling position with respect to a pre-selected test element, wherein in the sampling position the test system drives the actuator in order to perform the lancing motion of the pre-selected test element.

25. The test system according to claim 17, wherein the test element comprises at least one hydrophilic coating.

* * * * *